United States Patent [19]

Akkas et al.

[11] Patent Number: 4,735,610

[45] Date of Patent: Apr. 5, 1988

[54] DISPOSABLE SURGICAL FLUID HANDLING CASSETTE

[75] Inventors: Tamer Akkas, Irvine; Mark E. Steen, Chino Hills; John W. Berkman, Costa Mesa, all of Calif.

[73] Assignee: CooperVision, Inc., Palo Alto, Calif.

[21] Appl. No.: 850,047

[22] Filed: Apr. 10, 1986

[51] Int. Cl.[4] .............................................. A61M 1/00
[52] U.S. Cl. .................................... 604/119; 604/319
[58] Field of Search .................... 433/80, 94; 128/760; 604/22, 27, 30, 34, 35, 46, 48, 118, 119, 317, 319, 320

[56] References Cited

U.S. PATENT DOCUMENTS

| | | | |
|---|---|---|---|
| 3,191,600 | 6/1965 | Everett | 128/276 |
| 4,168,707 | 9/1979 | Douvas, Jr. et al. | 604/35 |
| 4,173,827 | 11/1979 | Austin, Jr. | 433/98 |
| 4,226,590 | 10/1980 | Hofmann | 433/95 |
| 4,493,695 | 1/1985 | Cook | 604/30 |

OTHER PUBLICATIONS

"CooperVision System VI", copyright 1984.

Primary Examiner—C. Fred Rosenbaum
Assistant Examiner—J. L. Kruter
Attorney, Agent, or Firm—Vorys, Sater, Seymour & Pease

[57] ABSTRACT

A surgical suction cassette for use with a microsurgical apparatus having a surgical handpiece connected by tubing with a control cabinet contains a tank to receive aspirated material from the microsurgical site, fluid connections for the tubes providing suction, pressure and irrigation fluid to the handpiece, fluid connections for connecting sources of pressure, vacuum and vent within the cabinet, fluid connection for an external source of irrigation fluid, and internal tubing providing connections between the connections to the handpiece and the connections to the cabinet. Solenoid actuated occluders in the cabinet compress the tubing in the cassette to turn the various fluid streams on and off. The cassette is provided with a drain for automatically removing the contents without changing the cassette. A latch hook, centrally located between the fluid connections to the cabinet holds the cassette in the cabinet when in use.

14 Claims, 18 Drawing Sheets

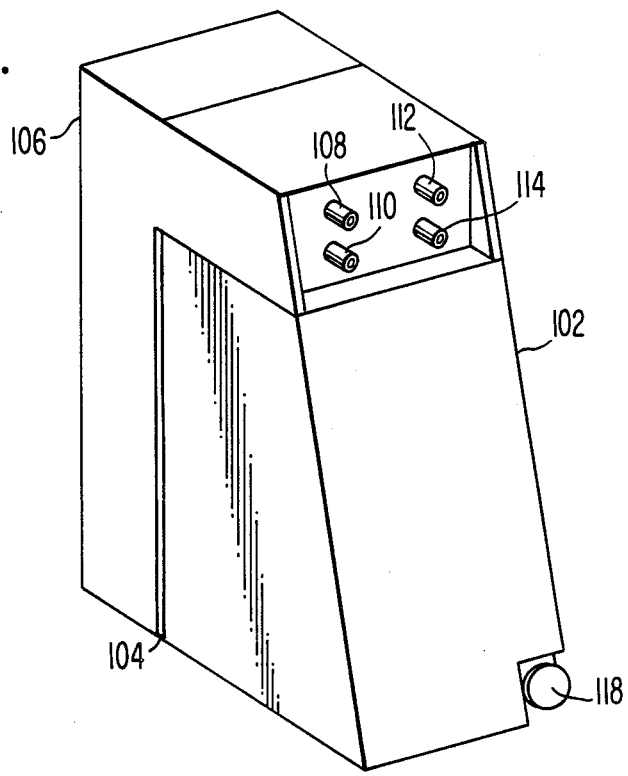
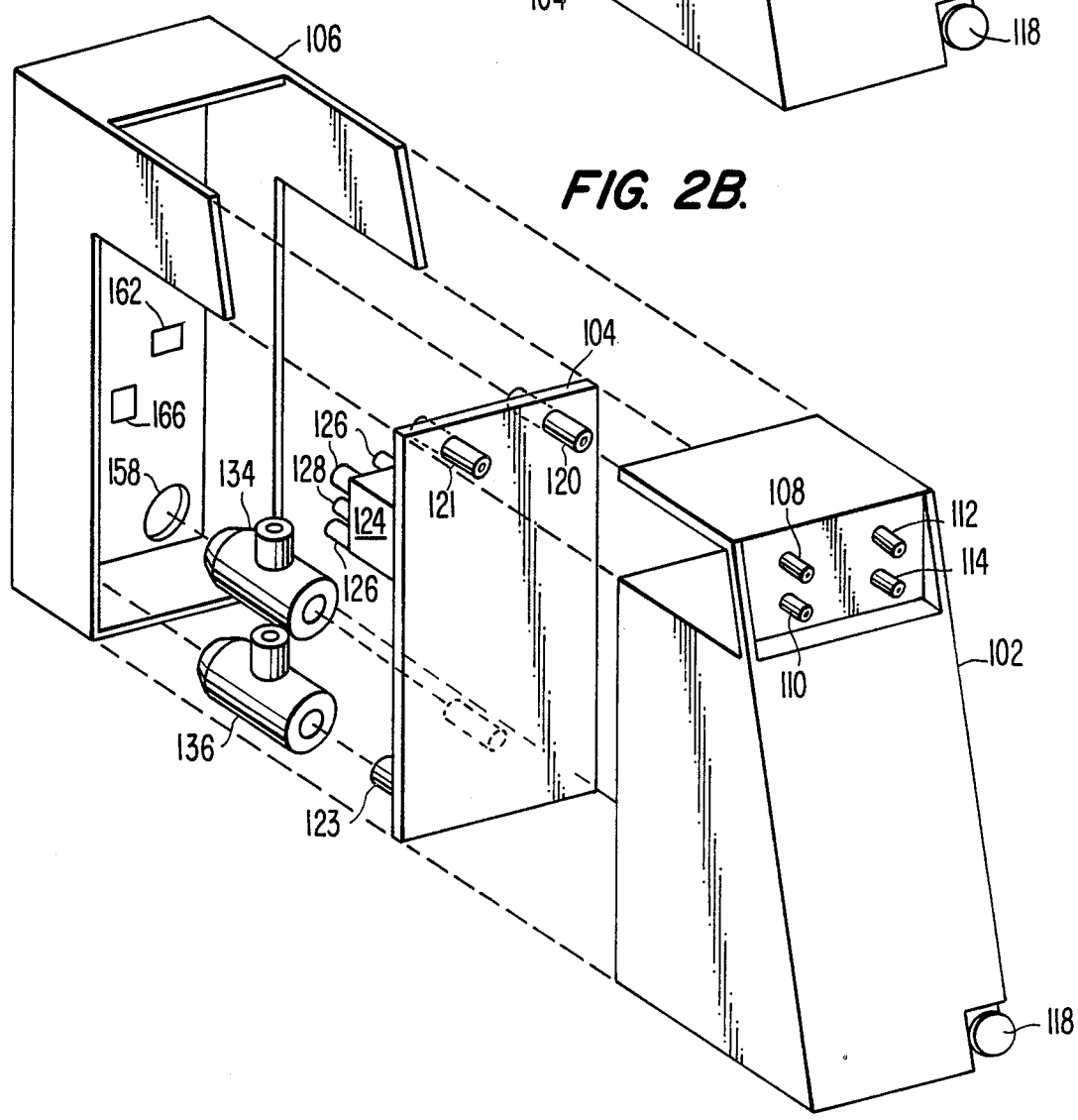

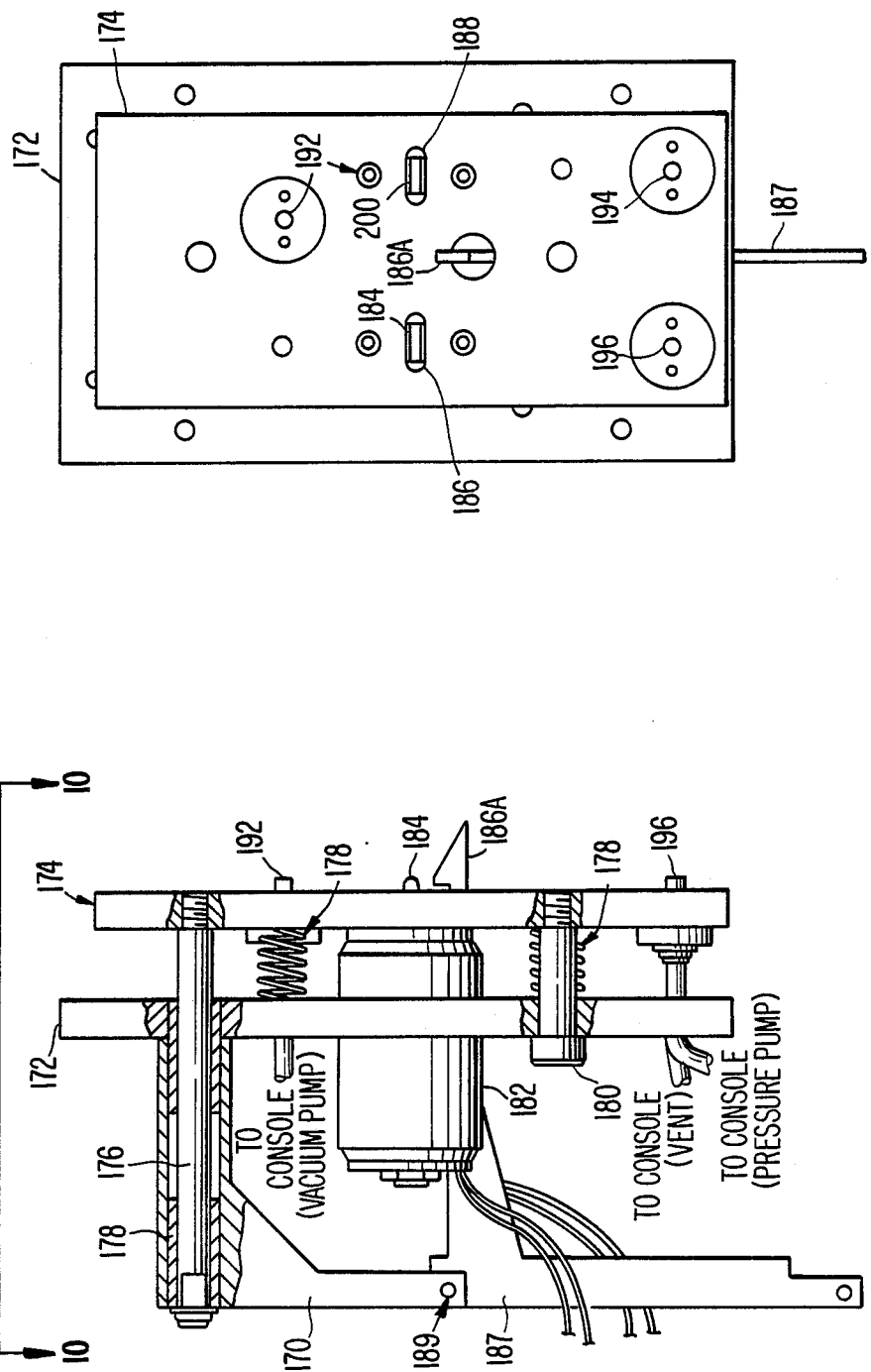

DISPOSABLE SURGICAL FLUID HANDLING CASSETTE

BACKGROUND OF THE INVENTION

1. Field of the Invention:

This invention relates to receptacles for surgical aspirators and more particularly to disposable containers adapted to receive fluids, tissue and the like aspirated from a surgical site by a surgical aspirator.

2. Description of the Prior Art:

Many intraocular surgical techniques have come to be performed by microsurgery using miniature surgical tools adapted to be inserted within the globe of the eye and provided with cutting means or severing intraocular tissue, suction means for removing this tissue by aspiration and irrigation means for bathing the surgical site in a physiolgial fluid and maintaining intraocular pressure. These microsurgical tools are powered and controlled by an electro-hydraulic and electro-pneumatic control system, which is actuated and controlled by the surgeon. Such a microsurgical system, for example, is the System VI manufactured by CooperVision, Inc.

In ophthalmological microsurgery the surgeon uses a handpiece which carries a small-diameter cylindrical surgical tool which is inserted into the eyeball through an incision made in the cornea or sclera. The surgical tool is commonly in the form of a hollow tube and may be provided with a pneumatically operated cutter for severing intraocular tissue. The central channel of the tubular surgical tool is connected to a source of suction which aspirates the severed tissue from the interior of the eyeball. In another embodiment, the surgical tool is comprised of coaxial tubes, and an ocular irrigation fluid is supplied through the outer tube to macerate and flush away tissue from the interior of the eye, while a source of suction is applied to the lumen of the internal tube in order to aspirate the tissue and fluid. In either case, the excised tissue which is aspirated from the interior of the eye, possibly together with fluid aspirated along with the tissue, is collected in a collection vessel of some sort, e.g., a bottle or bag, usually located remote from the handpiece and near the source of suction.

In order to control the operations of the microsurgical tool, a remote control cabinet or console is usually provided which contains a source of suction for the aspirating function of the surgical tool, a source of gas pressure to operate a pneumatically powered surgical cutter, a source of irrigation fluid and control means for controlling the supply of suction, fluid and pressure to the surgical handpiece. The fluid, pressure and/or suction is supplied to the surgical handpiece via flexible tubing connecting the handpiece with the control cabinet.

The control cabinet is also provided with switches for selecting the particular mode of operation of the microsurgical system and with control means to adjust the parameters of the system such as the level of the suction vacuum and the cutting rate of the microsurgical cutter. The control cabinet also contains means, e.g., solenoid controlled valves, for turning the fluid flow, suction, and gas pressure on and off. These control valves are actuated under control of the surgeon, generally through the operation of a footswitch.

Two common intraocular surgical procedures are vitrectomy and irrigation/aspiration (I/A). In vitrectomy, portions of the vitreous are severed by a pneumatically-operated reciprocating cutting and the severed tissue is aspirated by suction through the central lumen of the hollow tubular cutter. Accordingly, in vitrectomy procedures, the handpiece must be provided with a source of gas pressure for operating the cutter and with a source of suction for removing the excised tissue. In irrigation/aspiration procedures, the handpiece must also be provided with a source of irrigation fluid. In either case, the aspirated fluid and/or tissue must be collected in a suitable receptacle for disposal.

In any intraocular procedure which involves aspiration of fluid and/or tissue from the interior of the eyeball, it is evident that control of the level of suction is very important in order to prevent damage to the eyeball including possible collapse due to excessive suction. Control of the suction level is set by the surgeon using control means in the control cabinet. However, when the aspiration is shut off by valve means in the control cabinet a residual vacuum remains within the tubes and within the receptacle for aspirated fluid and tissue. Accordingly, when the suction is cut off the suction tube is immediately vented to the atmosphere by a solenoid control vent valve. Accordingly, the pressure within the suction tubes immediately rises to atmospheric pressure, and aspiration of material from within the eyeball is essentially terminated at once.

Because of the rather complex fluid connections required between the control cabinet and the handpiece of an ophthalmological microsurgical system, attempts have been made to simplify the connecting process by incorporating some of the fluid connection manifold within a cassette which incorporated both a collection vessel, means for connecting the various tubes leading to the handpiece and internal tubing connections for connecting and controlling the suction source, the vent, and the irrigation fluid. Such a microsurgical cassette is disclosed in Cook, U.S. Pat. No. 4,493,695. The microsurgical cassette receptacle therein disclosed fits into a location in the control cabinet where it is releasably held by a latch. The control cabinet has connectors for a source of suction and for a controlled vent valve which mate with corresponding connectors on the cassette. The control cabinet is also provided with controllable occluders which can press on the tubing manifold within the cassette to control the flow of irrigation fluid and to control the suction. However, this cassette does not include means for controlling gas pressure for powering a vitrectomy cutter. If the cassette becomes filled with aspirated material during the surgical procedure, the cassette must be replaced with an empty cassette or removed from the console, emptied and put back into the console. This process interrupts the operation.

Accordingly, a need has continued to exist for an improved surgical suction cassette.

SUMMARY OF THE INVENTION

These improvements have been achieved by a surgical fluid handling cassette for use with a microsurgical apparatus comprising
  a surgical handpiece,
  a control cabinet,
  a source of vacuum located within said control cabinet,
  a source of pressurized gas located within said control cabinet,
  a source of irrigation liquid, a suction line fluid conduit connecting said source of vacuum to said handpiece, a pressure line fluid conduit connecting said source of pressurized gas to said handpiece, and an irrigation line fluid conduit connecting said source of irrigation liquid to said handpiece, wherein the cassette comprises a vacuum tank, suction fluid coupling means mounted on the vacuum tank for connecting to said suction line, pressure fluid coupling means mounted on the tank for connecting to said pressure line, irrigation fluid outlet coupling means mounted on the tank for connecting to said irrigation line, vaccum fluid coupling means mounted on the tank for connecting to said source of vacuum, gas fluid coupling means mounted on the tank for connecting to said source of pressurized gas, irrigation fluid inlet coupling means mounted on the tank for connecting to said source of irrigation liquid, fluid conduit means connecting the vacuum fluid coupling means with said vacuum tank, fluid conduit means connecting the vacuum tank with said suction fluid couping means, fluid conduit means connecting the gas fluid coupling means with said pressure fluid coupling means, and fluid conduit means connecting the irrigation fluid inlet coupling means to irrigation fluid outlet coupling means.

In preferred embodiments, the fluid handling cassette contains vent fluid coupling means for connecting to a controlled vent within the control cabinet and a fluid conduit within the cassette for connecting the vent fluid coupling means to the fluid conduit connecting the vacuum tank to the suction fluid coupling. In a further preferred embodiment, the cassette contains a drain orifice in the vacuum tank for draining fluids when the tank becomes full or whenever drainage is required. A preferred drain mechanism is a drain tube connected to the drain orifice and having a check valve at the other end. The cassette does not have to be removed from the console to drain it.

Accordingly, it is an object of this invention to provide a cassette capable of serving as a receptacle for fluid and tissue aspirated from a microsurgical site.

A further object is to provide a microsurgical suction cassette having means for connecting and controlling a source of suction for a microsurgical handpiece.

A further object is to provide a microsurgical cassette having connecting means for connecting a source of gas pressure to the handpiece of a microsurgical instrument.

A further object is to provide a microsurgical cassette having means for conducting and controlling irrigation fluid from a source thereof to the handpiece of a microsurgical instrument.

A further object is to provide a microsurgical suction cassette having means to drain the cassette when it becomes full or whenever drainage is required without having to remove the cassette from the console.

A further object is to provide a microsurgical cassette having automatic drain means.

Further objects of the invention will become apparent from the description of the invention which follows.

BRIEF DESCRIPTION OF THE DRAWINGS

The invention will be more easily understood in connection with the following drawings.

FIG. 2A shows a perspective view of the microsurgical cassette of this invention.

FIG. 2B shows an exploded perspective view of the main structural components of the microsurgical cassette of FIG. 2A.

FIG. 8 is a side elevation view, partially cut away, of the cassette mounting and retaining mechanism in the control cabinet.

FIG. 9 is a front elevation view of the cassette mounting mechanism.

DETAILED DESCRIPTION OF THE INVENTION AND PREFERRED EMBODIMENTS

Figure 1A:
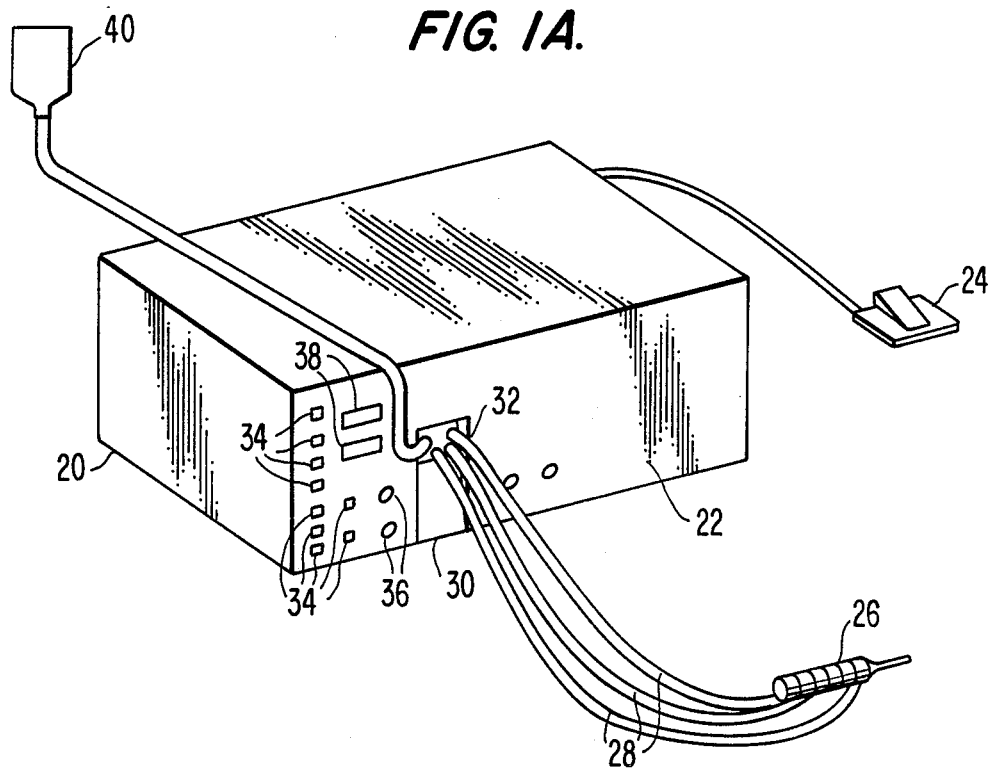
FIG. 1A is a perspective view of an ophthalmological microsurgical system of the type which uses the cassette of this invention, showing the cassette inserted into its location in the control cabinet of the microsurgical system and connected to a microsurgical handpiece and a source of irrigation fluid.

The invention will now be described in detail with reference to the various figures of the drawings wherein the reference characters refer to like parts in each of the figures.

FIG. 1A shows a general view of an ophthalmological microsurgical system which uses the disposable cassette of this invention. In this view are illustrated the control cabinet 20 which has a front panel 22 containing various switches and controls for the operation of the instrument, a footswitch 24 connected to the control cabinet 20 for actuating the various functions of the microsurgical instrument, and a handpiece 26 which is used by the surgeon in performing the surgery and is connected via a number of tubes 28 to the cassette 30 which is mounted in a recess 32 in the front panel. A number of switches 34, for example of the push-button type, are provided in order to select the various modes of operation of the machine, e.g., vitrectomy or irrigation/aspiration, and control knobs 36 are provided for adjusting the level of suction and the rate of cutting. Indicators 38 display the relevant operating conditions, e.g., preset suction vacuum and actual suction vacuum.

Figure 1B:
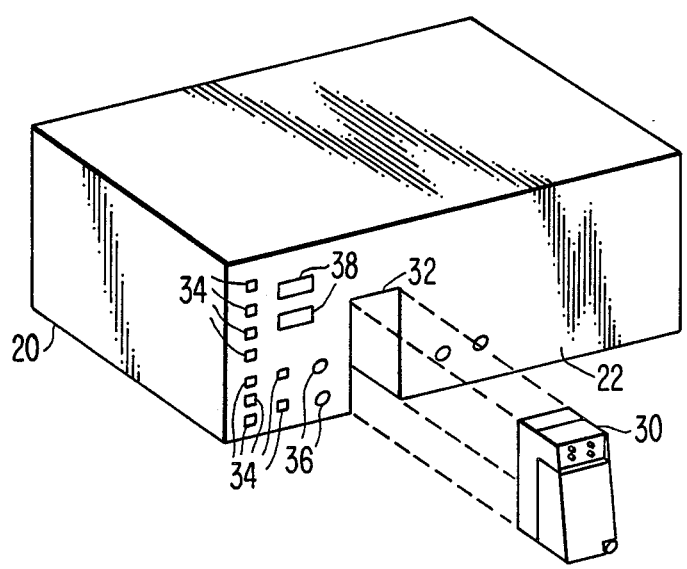
FIG. 1B shows the cassette of this invention separated from the control cabinet.

The cassette 30 is shown removed from its recess 32 in FIG. 1B. It is inserted directly into the recess 32 as shown by the lead lines and is received by a spring-loaded mounting plate where it is retained by a latch mechanism as is discussed in more detail below.

Turning now to FIGS. 2-7 which illustrate the cassette itself in more detail, the cassette generally comprises, as shown in the assembled view of FIG. 2A and the exploded view of FIG. 2B a vacuum tank 102, which is preferably molded of a transparent synthetic resin material, a valve plate 104 which is sealed to the rear of the vacuum tank to form a vacuum-tight enclosure, and a cover 106 which covers the valve plate and encloses the internal parts of the cassette. Located just above the vacuum tank 102 on the front of the cassette are nipples which serve as fluid couplings for connecting the various tubes leading to the handpiece. These include an irrigation inlet fluid coupling 108, an irrigation outlet fluid coupling 110, a suction fluid coupling 112 and a pressure fluid coupling 114. In the embodiment of the cassette intended for use in irrigation/aspiration procedures, all connections on the cassette are used, while in vitrectomy procedures only the suction fluid coupling 112 and the pressure coupling 114 are connected via tubing to the handpiece.

Figure 3A:
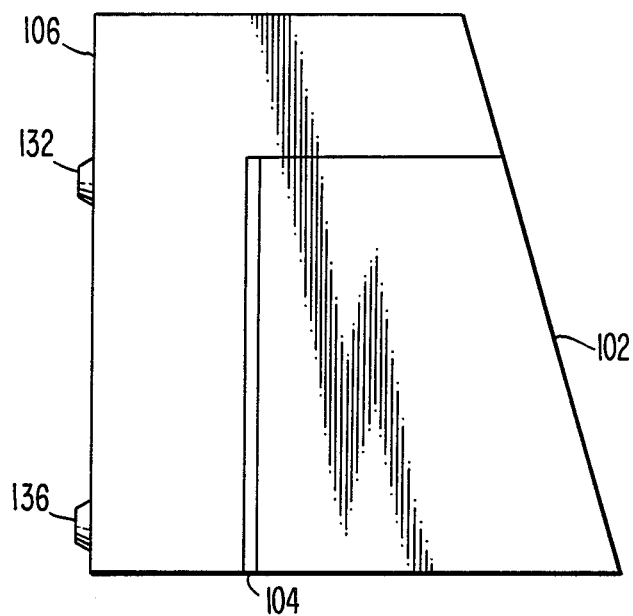
FIG. 3A shows a side elevation view of the cassette of this invention.
Figure 3B:
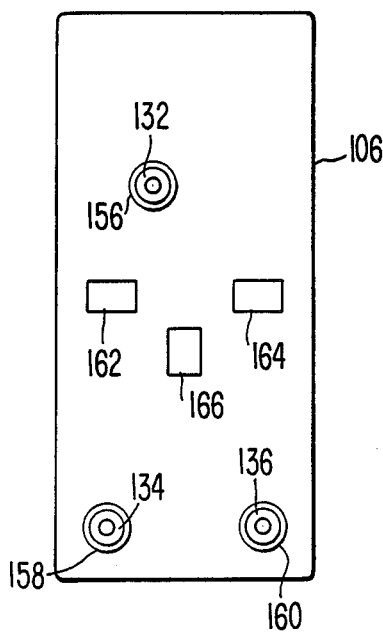
FIG. 3B shows a rear elevation view of the cassette of this invention.
Figure 3C:
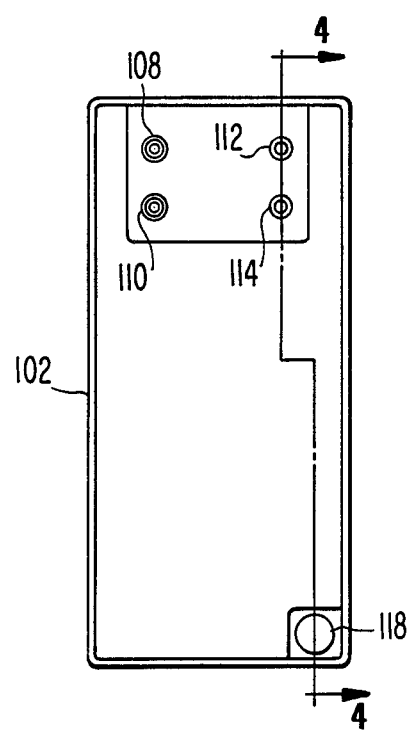
FIG. 3C shows a front elevation view of the surgical cassette of this invention.

FIG. 3A shows a side elevation view of the cassette. FIG. 3B shows a rear elevation showing various apertures in the cover which provide for the various functions of the cassette and are discussed in more detail below. FIG. 3C shows a front view of the cassette.

Figure 4:
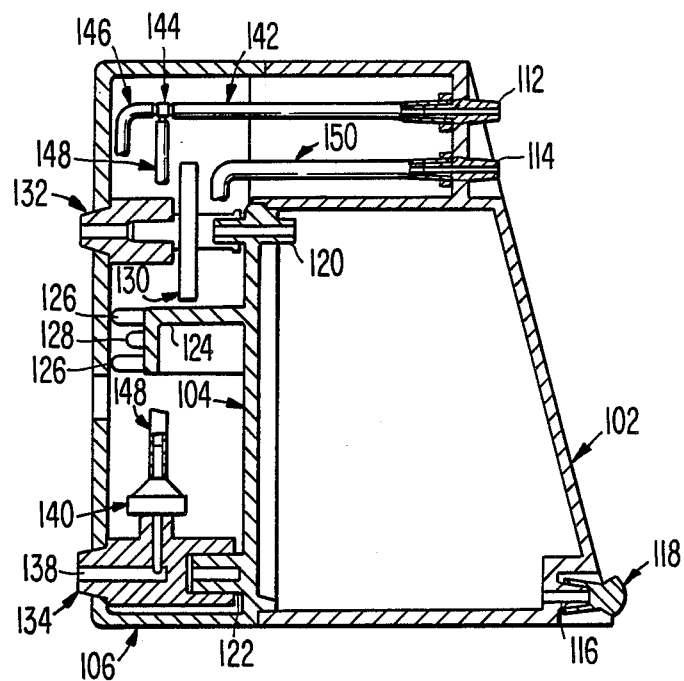
FIG. 4 is a sectional side elevation view taken along the line 4—4 in FIG. 3C, and viewed in the direction of the arrows on line 4—4, showing the internal tubing connected for I/A.

FIG. 4 is a section taken along line 4—4 in FIG. 3C, looking in the direction of the arrows on line 4—4. This figure shows the internal construction of the cassette with the internal tubing connected for use in I/A procedures. FIG. 4 shows the vacuum tank 102 provided with a drain orifice 116 which is ordinarily covered with a drain cap 118. The rear of the vacuum tank is sealed by the valve plate 104 which is provided with a vacuum orifice 120 for connecting the vacuum tank to a source of vacuum within the control cabinet and a fluid connection 121 (FIG. 5) for connecting the tank to the suction fluid coupling 112. The valve plate 104 also carries a support boss 122 for the vent angle grommet 134. A similar support boss (123, FIG. 2B) is provided on the valve plate 104 for the pressure angle grommet 136. A bracket 124 on the valve plate 104 carries occlusion bosses 128 which cooperate with solenoid actuated occluders to pinch the internal tubes of the cassette as discussed in more detail below, and tube guides 126 which confine the tubes in proper relation to the occlusion bosses 128.

Figure 5:
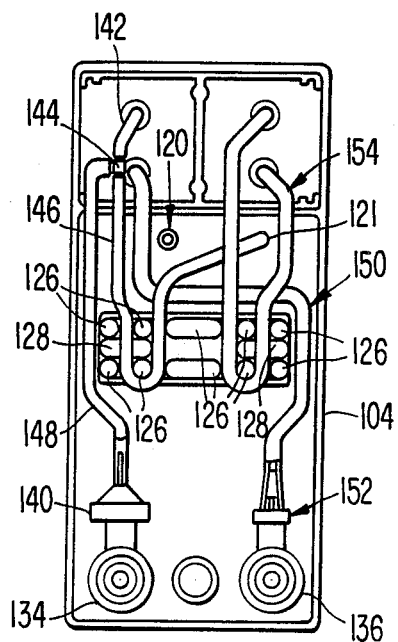
FIG. 5 is a rear elevation view of the embodiment of the cassette of this invention having the internal tubing connections arranged for I/A, with the cover removed so that the internal tubing connections can be seen.

The vacuum orifice 120 is provided with a filter 130 which protects the source of vacuum in the control cabinet from contamination by material aspirated into the vacuum tank 102. The filter is in turn connected to a linear grommet 132 which is made of an elastomeric material and is intended to mate with a connector on the control cabinet to connect the vacuum tank to the source of vacuum within the control cabinet. The vacuum line 142 connects the vacumm connection 112 with a tee-fitting 144 from which another vacuum line 146 runs to a vacuum connection on the vacuum tank 102. The stem of the tee-fitting 144 is connected to a vent tube 148 which is in turn connected to a check valve 140. The other side of the check valve is connected to angle grommet 134 which is also made of an elastomeric material adapted to seal with a connector on the mounting plate within the cabinet so that vent passage 138 is connected to a solenoid-controlled vent valve within the cabinet. Pressure connection 114 is internally connected via pressure tube 150 with the pressure angle grommet 136. No check valve is needed in this pressure line, but a connecting fitting 152 provides for connection between the pressure line 150 and the pressure angle grommet 136. As can best be seen in FIG. 5 the irrigation tube 154 passes between the tube guides and over the occlusion boss 128. A solenoid-actuated occluder mounted within the cabinet, shown in FIGS. 8-10 and described in more detail below, pinches the tube against the occlusion boss in order to shut off the flow of irrigation fluid under control of the surgeon. Similarly, the vacuum line 146 passes around the tubing guides 126 and across the occlusion boss 128 where it can be occluded by the action of a solenoid-actuated occluder in a similar way. Vacuum line 146 is then connected to vacuum fitting 121, as shown in FIG. 5.

The back of the cassette is covered by cover 106 which has a number of apertures to permit interaction between elements of the cassette and cooperating elements of the cabinet. These are illustrated in FIG. 3B. Holes 156, 158 and 160 allow the vacuum line grommet 132, the vent line grommet 134 and the pressure line grommet 136, respectively, to pass through the cover 106 to engage mating fittings on the cabinet. The edges of the holes cooperate with shoulders on the respective grommets to support the grommets between the cover 106 and the support bosses or connections on the valve plate 104. Apertures 162 and 164 are located over the occluding bosses 128 of the valve plate 104 and allow the solenoid-actuated occluders to pass through the cover 106 and pinch off the vacuum line 146 and the irrigation line 154, respectively. Aperture 166 receives the latch hook 186 which passes through the aperture 166 and catches the interior surface of the cover 106 to hold it securely in position in the cabinet. The holes 156, 158 and 160 for the grommets 132, 134 and 136 which make the vacuum fluid coupling, the vent fluid coupling and the pressure fluid coupling respectively, are located generally at the vertices of a triangle and the latch aperture 166 is located generally centrally within this triangle. This central location of the latch aperture 166 is an advantage of the cassette of this invention for it permits a central application of the force which holds the cassette in the cabinet and seals the connections for the vacuum, vent and pressure lines. This central application of the retaining force balances the holding and sealing force relatively uniformly among the three fluid connectors, and thereby contributes to a uniform and effective sealing action at these three connectors. This balanced distribution of forces also holds the cassette securely in position to receive the force exerted by the occluders in pinching the internal tubing against the occluding bosses 128.

Figure 6:
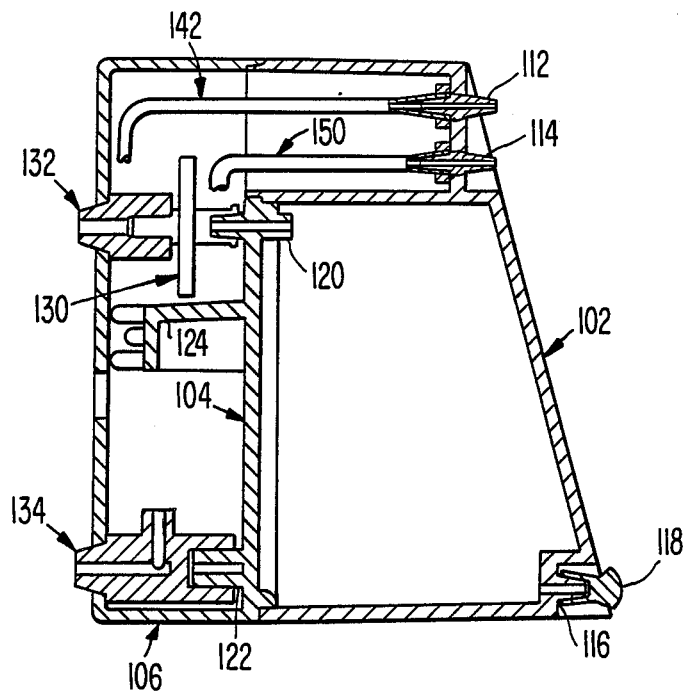
FIG. 6 is a side sectional elevation view taken along the same line as in FIG. 4, but with the internal tubing connected for use in vitrectomy.
Figure 7:
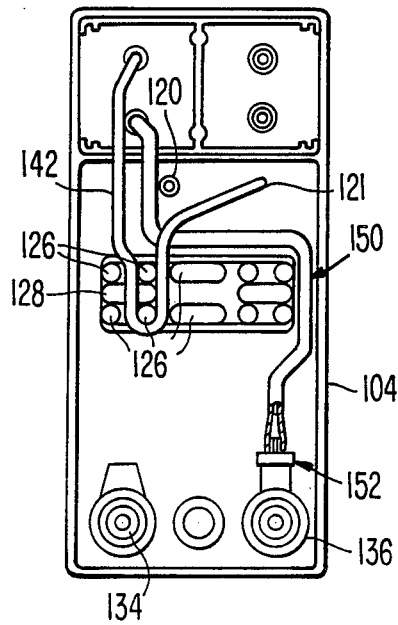
FIG. 7 is a rear elevation view of the cassette of this invention arranged for use in vitrectomy procedures wherein the rear cover has been removed in order to show the internal tubing connections.

FIGS. 6 and 7 show an embodiment of the cassette of the invention arranged for use in vitrectomy procedures. The parts of the cassette are the same as that used for I/A, but the internal tubing is somewhat simpler, since the irrigation function is not used. The pressure line 150 is connected via the connection fitting 152 to the pressure angle grommet 136. The vacuum line 142 in this embodiment passes between the tube guides 126 and over the occlusion boss 128 and thence to the vacuum tank connection just as it does in the I/A embodiment of the cassette. There is no line connecting to angle grommet 134 in this cassette configuration.

Figure 10:
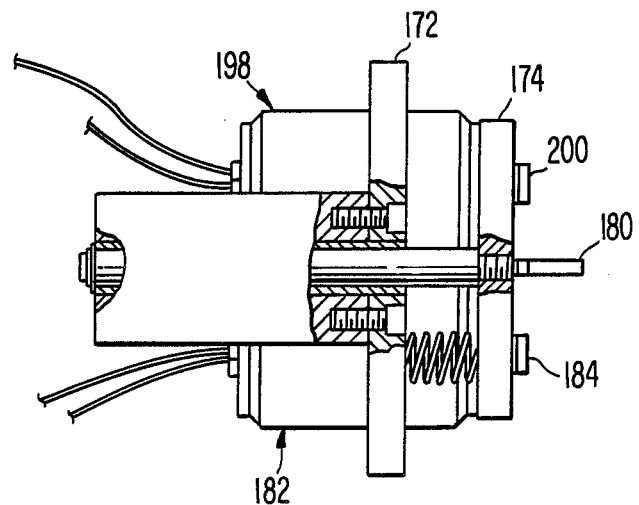
FIG. 10 is a top view, partially cut away, of the cassette mounting mechanism in the cabinet.

FIGS. 8-10 shows the mechanism which receives and retains the cassette within the control cabinet. FIG. 10 8 is a side elevation, partly cut away; FIG. 9 is a front elevation; FIG. 10 is a top view taken as shown by the line 10—10 in FIG. 8 looking in the direction of the arrows on line 10—10. The cassette support and retaining mechanism comprises a mounting frame 170 which supports a mounting plate 172. A pressure plate 174, which receives the back surface of the cassette cover is resiliently mounted on the mounting plate and frame by means of a guide 176 received within a bushing 178 retained within the frame 170. The pressure plate is urged away from the mounting plate 172 by springs 178, and the outward travel of the pressure plate 174 is limited by the stop 180. The pressure plate 174 also carries an occluder solenoid for irrigation 182 with its occluder 184 which passes through an aperture 186 in the pressure plate 174 and corresponding aperture 164 in the cassette cover 106 to pinch the irrigation tubing 154 within the cassette against the occlusion boss 128 as discussed above. Similarly, also mounted on the pressure plate 174 is an occluder solenoid 198 for the vent line together with its occluder 200 which projects through an aperture 188 in the pressure plate 174 and corresponding aperture 162 in the cassette cover 106 to pinch the vacuum line 146 within the cassette. The pressure plate 174 also carries friction-fit fluid connectors which mate with the grommets of the cassette to provide connections for the pressure, vacuum, and vent lines. Thus, connector 192 provides a connection between the source of vacuum in the cabinet and the vacuum tank of the cassette. Connector 194 provides a connection between the vent line in the cassette and the solenoid-actuated vent valve within the cabinet. Connector 196 provides a connection between the pressure line in the cassette and the source of gas pressure within the cabinet. Latch hook 186A is a part of latch 187 which is pivotably attached to frame 170 at pivot 189. Latch hook 186A is kept in the latching position as shown by spring means not shown and is moved downward to the cassette release position by pressure on latch 187.

Figure 11A:
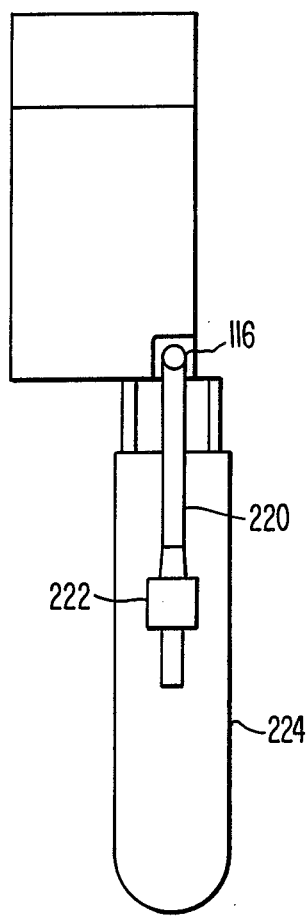
FIG. 11A shows a front elevation view of the cassette of this invention connected to an automatic drain mechanism.
Figure 11B:
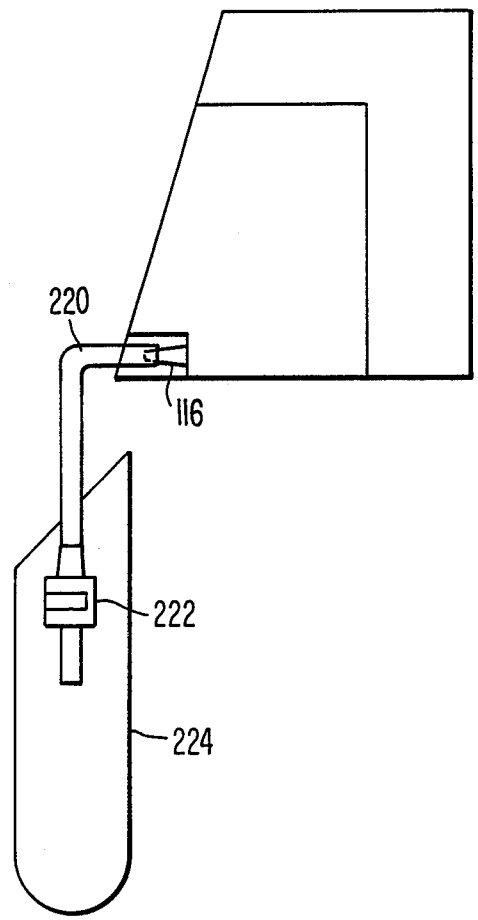
FIG. 11b shows a side elevation view of the cassette connected to the drain mechanism.

FIG. 11A and FIG. 11B illustrate the automatic drain embodiment of the invention wherein one end of a drain tube 220 is connected to drain orifice 116 and the other end of the drain tube 220 is connected to a check valve 222 which permits outflow of fluid from the vacuum tank but does not permit backward flow from the exterior into the vacuum tank. The automatic drain works as follows. When the aspiration function of the handpiece is turned off and the vent is opened to break the vacuum in the tank and aspiration tubing, the pressure within the tank becomes equal to the outside atmospheric pressure. Under these conditions the liquid within the vacuum tank can drain freely by gravity through the drain tube 220 and the check valve 222 into the exterior receptacle 224. When the suction is turned on again, the pressure within the vacuum tank drops and the check valve 222 closes to prevent reverse flow into the vacuum tank of the cassette. This automatic drain feature provides uninterrupted surgery even when very large amounts of fluid are aspirated into the cassette.

Figure 12:
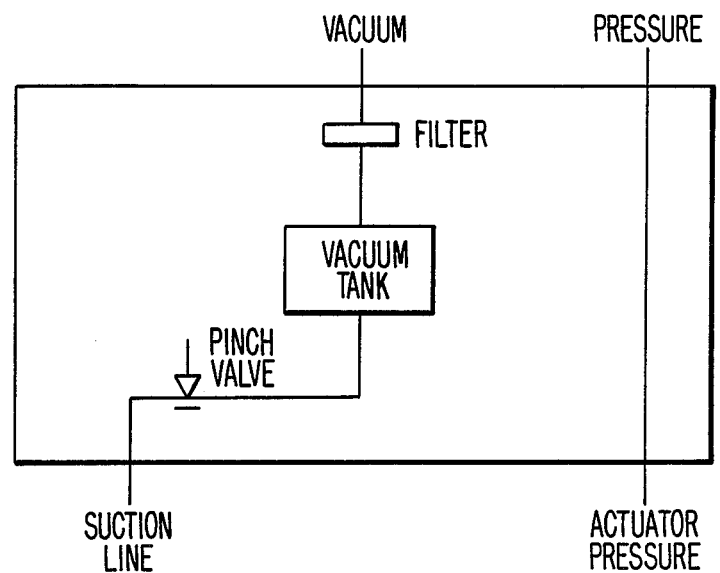
FIG. 12 is a schematic diagram showing the fluid connections of the cassette of this invention as arranged for vitrectomy.

FIG. 12 is a schematic drawing of the pneumatic connections and operation of the cassette of this invention when the interior tubing is connected for vitrectomy. The cassette 30 is represented by the rectangular box surrounding the components of the pneumatic plumbing. The pressure source in the cabinet is connected to the pressure line in the cassette and the pressure connection on the front of the cassette is connected to the pressure line going to the handpiece. The vacuum source in the cabinet, which may be a vacuum pump of a type conventionally used in ophthalmological surgery, e.g., a peristaltic vacuum pump, is connected to the vacuum connection on the cassette. The vacuum line contains a filter to prevent material from the vacuum tank from entering the vacuum line to the cabinet. The vacuum tank is connected to the suction port of the cassette via an internal tube which is acted on by the occluder to form a pinch valve. As soon as the surgeon stops the suction, generally by releasing pressure on the footswitch, the occluder pinches off the vacumm line.

Figure 13:
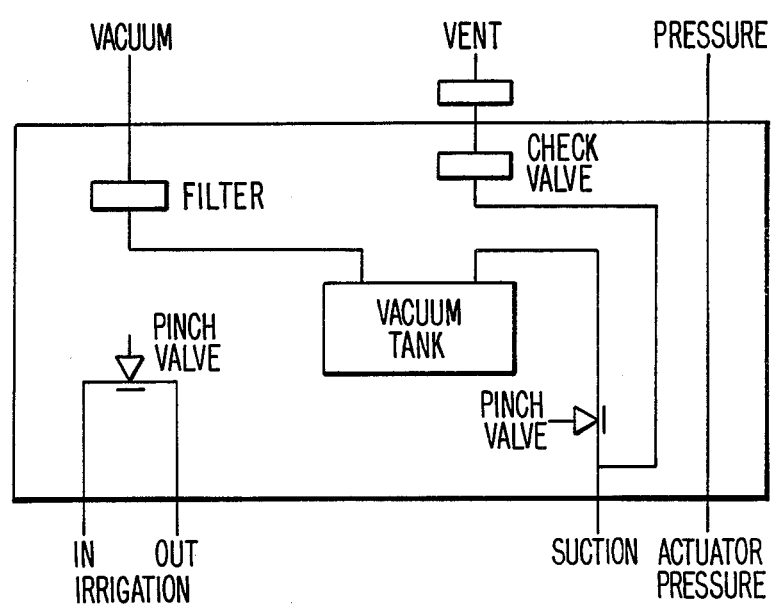
FIG. 13 is a schematic diagram of the cassette of this invention as arranged for irrigation/aspiration procedures.

FIG. 13 is a schematic drawing of the pneumatic connections and operation of the cassette of this invention when it is connected for I/A procedures. The vacuum connections between the vacuum pump in the cabinet and the vacuum tank are the same as in the vitrectomy cassette, as are the connections for the pressure line. Similarly, the vacuum pinch valve, actuated by the vacuum occluder, closes the tube between the vacuum tank and the suction line when the surgeon releases the footswitch. In this embodiment a tee-connection in the suction line permits the vent line to release the vacuum in the suction line immediately. The check valve in the vent line prevents aspirated fluid from reaching the solenoid-controlled vent valve. A separate irrigation line within the cassette is connected to a source of irrigation fluid and to the irrigation tube leading to the handpiece. An irrigation occluder operates against the irrigation line to pinch it off when the instrument is not actuated by the surgeon.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. For an ophthalmic microsurgical system including a surgical handpiece having an aspiration function, a remote control cabinet operatively connected to the surgical handpiece, a source of vacuum associated with the cabinet, a source of pressurized fluid associated with the cabinet, and a vent valve associated with the cabinet, a surgical fluid handling cassette comprising:

a vacuum tank, a suction fluid connecting means connected to said tank for connecting said tank to the source of vacuum, a suction means fluid connecting means for connecting said vacuum tank to the handpiece, a vacuum fluid connecting means for connecting said vacuum tank to the source of vacuum for causing a vacuum in said vacuum tank and for sucking fluid from the handpiece through said suction fluid connecting means into said vacuum tank, a pressure fluid connecting means connected to said vacuum tank for connecting the source of pressurized fluid to the handpiece, a vent connecting means for connecting said vacuum tank to the vent valve for venting the vacuum from said vacuum tank, said vacuum tank including a drain orifice at a lower locating thereon and out through which fluid in said vacuum tank can gravity flow, and a draining means for automatically draining the fluid in said vacuum tank aspirated from the handpiece out said drain orifice, when the aspiration function of the handpiece is turned off and the vent valve is opened bringing the pressure in said vacuum tank up to generally the outside atmospheric pressure, said draining means comprising a drainage receptacle, a tubing means for providing a fluid connection from said drain orifice to said drainage receptacle, and a preventing means for preventing the flow of fluid from said drainage receptacle into said vacuum tank.

2. The surgical fluid handling cassette of claim 1 wherein said preventing means prevents the flow of fluid into said vacuum tank through said tubing and said drain orifice.

3. The surgical fluid handling cassette of claim 2 wherein said receptacle is positioned lower than said drain orifice.

4. The surgical fluid handling cassette of claim 2 wherein said preventing means comprises a check valve positioned in said tubing means.

5. The surgical fluid handling cassette of claim 2 wherein said preventing means blocks the flow of aspirated fluid from said receptacle to said drain orifice when the aspiration function of the handpiece is operating.

6. The surgical fluid handling cassette of claim 2 wherein said receptacle is positioned lower than said drain orifice, said preventing means comprises a check valve positioned in said tubing means, and said preventing means blocks the flow of aspirated fluid from said receptacle to said drain orifice when the aspiration function of the handpiece is operating.

7. The surgical fluid handling cassette of claim 6 further comprising an irrigation fluid connecting means connected to said vacuum tank for connecting the handpiece to a source of irrigation fluid.

8. The surgical fluid handling cassette of claim 1 further comprising a valve plate attached to the rear of said vacuum tank.

9. The surgical fluid handling cassette of claim 8 wherein said valve plate is sealed to said vacuum tank to form a vacuum-tight enclosure.

10. The surgical fluid handling cassette of claim 8 further comprising a cover plate covering said valve plate.

11. The surgical fluid handling cassette of claim 1 further comprising a latch hook mounting means for releasably mounting said vacuum tank in a recess of the control cabinet, said latch hook mounting means including a centrally-located latch aperture adapted to receive a spring-biased latch hook therein.

12. The surgical fluid handling cassette of claim 1 wherein said suction fluid connecting means comprises a suction tubing and a pinch valve on said suction tubing.

13. The surgical fluid handling cassette of claim 1 wherein said vent connecting means includes a connecting means connected to said vacuum tank for connecting the vent valve to the suction line between said suction fluid connecting means and the handpiece and permitting the release of the vacuum in the suction line.

14. The surgical fluid handling cassette of claim 1 further comprising an irrigation fluid connecting mean connected to said vacuum tank for connecting the handpiece to a source of irrigation fluid.

* * * * *